(12) United States Patent
Rayment et al.

(10) Patent No.: US 8,747,830 B2
(45) Date of Patent: Jun. 10, 2014

(54) WOUND REPAIR COMPOSITION AND METHOD

(75) Inventors: Erin A. Rayment, Brisbane (AU); Tim Dargaville, The Gap (AU); Zee Upton, Brisbane (AU)

(73) Assignee: Queensland University of Technology, Brisbane (AU)

( * ) Notice: Subject to any disclaimer, the term of this patent is extended or adjusted under 35 U.S.C. 154(b) by 650 days.

(21) Appl. No.: 12/663,438

(22) PCT Filed: Jun. 10, 2008

(86) PCT No.: PCT/AU2008/000828
§ 371 (c)(1),
(2), (4) Date: Feb. 11, 2010

(87) PCT Pub. No.: WO2008/148174
PCT Pub. Date: Dec. 11, 2008

(65) Prior Publication Data
US 2010/0172860 A1    Jul. 8, 2010

(30) Foreign Application Priority Data
Jun. 8, 2007   (AU) ................................ 2007903101

(51) Int. Cl.
*A61K 31/74* (2006.01)

(52) U.S. Cl.
USPC ..................................................... 424/78.06

(58) Field of Classification Search
CPC .............................................. A61K 47/48176
USPC ..................................................... 424/78.06
See application file for complete search history.

(56) References Cited

U.S. PATENT DOCUMENTS

| | | | | |
|---|---|---|---|---|
| 4,209,605 A | * | 6/1980 | Hoy et al. ........................ | 528/54 |
| 4,898,908 A | * | 2/1990 | Lahalih et al. .................. | 524/593 |
| 5,115,801 A | * | 5/1992 | Cartmell et al. ................. | 602/48 |
| 5,652,227 A | * | 7/1997 | Teronen et al. .................. | 514/75 |
| 6,320,011 B1 | * | 11/2001 | Levy et al. ....................... | 528/72 |
| 8,101,196 B2 | * | 1/2012 | Luthra et al. ................... | 424/422 |
| 2004/0213758 A1 | | 10/2004 | Sefton et al. | |

FOREIGN PATENT DOCUMENTS

| | | |
|---|---|---|
| EP | 0635733 | 9/1999 |
| GB | 2408207 | 5/2005 |
| WO | 02/40058 | 5/2002 |
| WO | 2004/011043 | 2/2004 |
| WO | 2006-002506 | 1/2006 |
| WO | 2006-126926 | 11/2006 |

OTHER PUBLICATIONS

International Search Report dated Mar. 31, 2008, in Application No. PCT/AU2008/000828.
Written Opinion dated Jan. 22, 2009, in Application No. PCT/AU2008/000828.
International Preliminary Report on Patentability dated Sep. 30, 2009, in Application No. PCT/AU2008/000828.
Ulrich D. et al. "Effect of Chronic Wound Exudates and MMP-2/9 Inhibitor on Antiogenesis In-Vitro" Plast. Reconstr. Surg. Aug. 2005, 116(2):539-45.
Lobermann R. et al. "Expression of matrix metalloproteinases and growth factors in diabetic foot wounds treated with a protease absorbent dressing" J. Diabetes Complications. Sep.-Oct. 2006, 20(5):329-35.
Tengvall P. et al. "Surface immobilized bisphosphonate improves stainless-steel screw fixation in rats" Biomaterials. May 2005, 25(11):2133-8.
Boateng, Matthews, Stevens & Eccleston, "Wound Healing Dressings and Drug Delivery Systems: A Review" Journal of Pharmaceutical Sciences, Aug. 8, 2008, vol. 97, No. 8, pp. 2892-2915.

* cited by examiner

*Primary Examiner* — Jake Vu
(74) *Attorney, Agent, or Firm* — Tarolli, Sundheim, Covell & Tummino LLP

(57) ABSTRACT

The invention provides a dressing composition comprising a bisphosphonate matrix metalloproteinase (MMP) inhibitor covalently bound to a polymer wherein, when the dressing is contacted with a wound, substantially all of the bisphosphonate remains with the dressing composition and is unable to enter the wound tissue. The invention also provides for a method of treatment of a wound by contacting a dressing composition comprising a covalently bound MMP inhibitor with the wound fluid to thereby selectively inhibit one or more MMP's in the wound fluid without inhibiting those in the wound tissue.

18 Claims, 4 Drawing Sheets

WOUND REPAIR COMPOSITION AND METHOD

CROSS-REFERENCE TO RELATED APPLICATIONS

The present application is a U.S. National Phase patent application under 35 U.S.C. §371 of International Application No. PCT/AU2008/000828, filed Jun. 10, 2008, which claims priority to Australian Patent Application No. 2007903101, filed Jun. 8, 2007, both of which are expressly incorporated herein by reference.

FIELD OF THE INVENTION

The present invention relates to wound healing. More particularly, the present invention relates to the use of covalently bound MMP inhibitors to promote the healing of chronic wounds.

BACKGROUND OF THE INVENTION

The treatment of chronic wounds represents a significant burden on the healthcare system. Currently, between 1-3% of the population in Australia suffer from chronic wounds which translates to a healthcare cost of upwards of $500 million per annum.

Chronic wounds can have a debilitating effect on sufferers and impacts negatively on their quality of life. The treatment of pain related to the wound is often identified as one of the main priorities in chronic wound management. In extreme cases amputation of the affected limb is necessary.

There is currently no single accepted treatment for chronic wounds. Topical treatments using growth factors have been shown to be only partially effective. It has been suggested that this kind of treatment has had limited success due to the high levels of proteases found in the chronic wound fluid resulting in degradation of the growth factors. Matrix metalloproteinases (MMP's) in particular are found in high levels in chronic wound fluid and they have been held responsible for the degradation of the extracellular matrix as well as key factors, including growth factors, critical to wound healing. To address this, some treatments have focused on inhibiting one or more MMP's to reduce the proteolytic environment.

U.S. Pat. No. 5,652,227 discloses the use of bisphosphonates as MMP inhibitors to reduce the excessive degradation of connective tissue matrix protein components in mammals. Inhibition of MMP-1 and MMP-8 using clodronate is stated as particularly desirable. The bisphosphonate is delivered orally, intravenously, or topically i.e. the intention is to make the bisphosphonate available systemically as well as to the wound tissue and wound fluid.

PCT publication WO 2006/126926 teaches that a suture thread with an MMP inhibitor adhered to it may be useful to prevent weakening or softening of the tissue surrounding the sutures after surgery. The inhibitor may be adhered to the suture thread by adsorption, electrostatic interaction or covalent bonding. The aim of this invention is, therefore, to have MMP inhibitors in direct contact with the tissue which is sutured to inhibit tissue degradation and so, loosening of the sutures.

Local contact between the tissue and inhibitor is favoured over systemic delivery. However, it is stated as being desirable that the MMP inhibitor should be gradually released from a fibrinogen matrix associated with the suture thread and so a combination of covalent and electrostatic loading is the preferred means of adherence to the suture thread. A large proportion of the MMP inhibitor is therefore to be released into the tissue in and around the wound.

WO 2002/40058 discloses a bisphosphonate covalently bound to a polymer such as poly(ethylene glycol) which also has a biologically active agent bound via a degradable linker. The bisphosphonate in this invention is employed solely for its hydroxy-apatite targeting ability.

The bisphosphonate is used to target the polymer to bone surfaces and as the degradable linker degrades the biologically active agent is released. This allows the bone surface to be used as a reservoir for a releasable biological agent. The bisphosphonate is present purely as a targeting moiety which is made available systemically via a number of possible delivery routes.

It has been reported that the role of MMP's in chronic wounds may not be as simple as was first thought and the destructive role they play in creating the proteolytic environment of the wound fluid may only represent part of the picture.

SUMMARY OF THE INVENTION

Some MMP's in the wound tissue have been shown to have a number of important roles in processes such as growth factor activation and immune system regulation in the wound bed which are important steps in wound healing. The approaches of the prior art mean that all MMP's, in both the wound fluid and wound bed, are exposed to the MMP inhibitor and this does not represent the best way to achieve normal healing.

The inventors have identified a need for an effective treatment of wounds. In one particular form, the present invention allows for the use of an MMP inhibitor which is covalently attached to a polymer as part of a wound dressing composition to be applied to the wound. This will ensure that MMP's in the chronic wound fluid are inhibited, thereby reducing the proteolytic content of the fluid, while those in the wound bed which are required for normal healing are not affected or are affected to a substantially lesser degree.

In one form, which is not necessarily the only or broadest form, the invention provides a dressing composition comprising an MMP inhibitor covalently bound to a polymer, whereby a major proportion of the MMP inhibitor remains bound to the dressing and is unable to enter the wound tissue.

A first aspect of the invention resides in a dressing composition comprising a bisphosphonate and/or derivatives or pharmaceutically acceptable salts thereof covalently bound to a polymer wherein, when the dressing is contacted with a wound, substantially all of the bisphosphonate remains with the dressing and is unable to enter the wound tissue.

Suitably, the bisphosphonate is an amino-bisphosphonate. Preferably, the amino-bisphosphonate is alendronate.

Suitably, the polymer is a hydrogel polymer. Typically, the hydrogel polymer comprises poly(2-hydroxyethyl methacrylate). Preferably, the hydrogel polymer comprises poly(2-hydroxyethyl methacrylate) and poly(ethyleneglycol).

If required, the bisphosphonate is covalently bound to a monomer which is incorporated into the polymer. Suitably, the monomer is selected from the group consisting of acrylates, methacrylates, vinyl sulfones or poly(ethylene glycol) aldehydes. Preferably, the monomer is methacryloyl chloride.

A second aspect of the invention resides in a method of producing a dressing composition including the step of covalently bonding a bisphosphonate to a polymer to thereby produce said dressing composition.

A third aspect of the invention resides in an MMP inhibitor-monomer conjugate comprising an MMP inhibitor coupled to a monomer.

Suitably, the MMP inhibitor is alendronate.

Preferably, the monomer is methacryloyl chloride.

A fourth aspect of the invention resides in a method of producing an MMP inhibitor-monomer conjugate including the step of coupling an MMP inhibitor with a monomer to thereby form an MMP inhibitor-monomer conjugate.

A fifth aspect of the invention resides in a dressing composition with an MMP inhibitor-monomer conjugate coupled thereto.

A sixth aspect of the invention resides in a method of selectively inhibiting an MMP within a wound fluid without inhibiting an MMP within a wound tissue, in a patient in need of such treatment, including the step of contacting the wound fluid with an MMP inhibitor covalently bound to a polymer in a dressing composition to thereby selectively inhibit said MMP within the wound fluid without inhibiting said MMP within the wound tissue.

Preferably, the MMP being inhibited within the wound fluid is MMP-9.

A seventh aspect of the invention resides in a method of therapeutic treatment of a wound in an animal including the step of administering a dressing composition of the first or third aspects to the animal.

Preferably, the animal is a mammal.

More preferably, the animal is a human.

Throughout this specification, unless the context requires otherwise, the words "comprise", "comprises" and "comprising" will be understood to imply the inclusion of a stated integer or group of integers but not the exclusion of any other integer or group of integers.

DETAILED DESCRIPTION OF THE INVENTION

Figure 1:
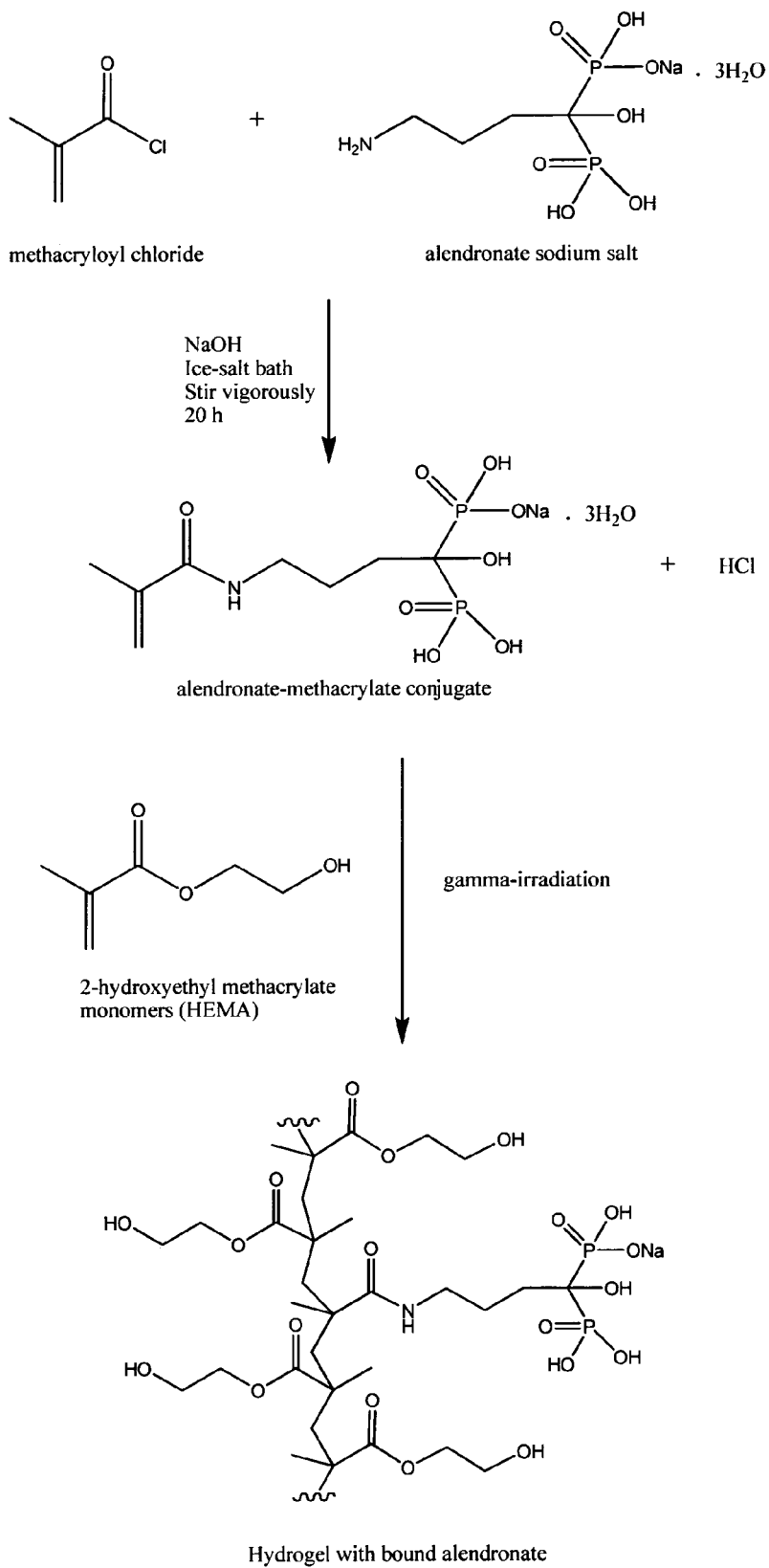
FIG. 1 shows the reaction of alendronate with methacryloyl chloride to form a conjugate and its inclusion into a pHEMA polymer.

One aspect of the invention resides in a dressing composition comprising a bisphosphonate and/or derivatives or pharmaceutically acceptable salts thereof covalently bound to a polymer wherein, when the dressing is contacted with a wound, substantially all of the bisphosphonate remains with the dressing and is unable to enter the wound tissue.

In a particular embodiment, the wound is a chronic wound.

The term "chronic wound" as used herein generally describes any break, or ulceration, of the skin that is of long duration or recurs frequently or that fails to progress through an orderly and timely sequence of repair.

The term "substantially all" as used herein to describe the amount of MMP inhibitor, e.g. bisphosphonate, which remains with the dressing composition means 80% or more of the MMP inhibitor remains bound. In particular embodiments this includes 80%, 85%, 90%, 91%, 92%, 93%, 94%, 95%, 96%, 97%, 98%, 99% and 100%.

While not wishing to be bound by any particular theory, it has been found that elevated levels of MMP's are present in the wound fluid of chronic wounds compared to that of acute wounds and this contributes greatly to the proteolytic environment of the wound which is extremely hostile for growth factors and connective tissue protein assembly necessary for normal healing. The inventors have shown that MMP-9 is the predominant MMP responsible for collagen degradation in chronic wound fluid.

It has been shown that a decreased level of active MMP's found in biopsies from the wound bed led to the chronicity of non-healing wounds. MMP levels have also been demonstrated to be significantly decreased in fibroblasts isolated from the chronic wound bed. It is therefore believed that these MMP's play a role in normal healing of the wound tissue. Introducing MMP inhibitors into a wound whereby they are free to diffuse into the wound tissue and systemic circulation as well as contacting the wound fluid, such as in existing treatments, does not, therefore, provide the best control of the factors responsible for wound healing.

A solution to this problem, presented herein, is to inhibit the MMP's in the chronic wound fluid responsible for collagen matrix and growth factor degradation while ensuring that the MMP inhibitor employed is substantially unable to diffuse or otherwise travel into the wound bed and surrounding tissues so that appropriate levels of active MMP's may be maintained in the wound bed for normal healing.

This is achieved by the provision of a wound dressing composition to which one or more MMP inhibitors are covalently bound. The dressing will contact the chronic wound fluid and the MMP's therein will be inhibited. In this manner the proteolytic environment of the chronic wound fluid is controlled to promote formation of the collagen matrix, and so, healing. Since the one or more MMP inhibitors are covalently bound they are not substantially released into the wound bed and so the levels of active MMP's in that tissue necessary for normal healing can be maintained. An improved healing environment is thus achieved on the surface of the wound without the disruption of the normal healing mechanisms in the wound tissue.

It should, therefore, be understood that the bound MMP inhibitor will inhibit, suppress, inactivate or in some manner reduce the activity of one or more MMP's in the wound fluid preferentially to inhibiting, suppressing, inactivating or in some manner reducing the activity of one or more MMP's in the wound tissue.

The term "wound fluid" will be understood by those of skill in the art as describing the wound exudate, being the fluid rich in protein and cellular elements which has seeped out of blood vessels and has been deposited on the wound tissue.

The terms "wound tissue" and "wound bed" will be understood to include the upper cellular layers of the wound exposed to the atmosphere as well as deeper cellular layers involved in tissue regeneration and other healing processes.

When the wound dressing contacts the wound fluid the fluid may be drawn into the dressing. This is particularly desirable since, as more wound fluid is drawn away from the wound bed, more of the MMP's therein will be inhibited by contacting the MMP inhibitor within the dressing. This also means the MMP inhibitor does not necessarily need to be placed in intimate contact with the wound bed to ensure the MMP's in the wound fluid are inhibited and so there is less chance of MMP's in the upper cellular layers of the wound bed being inadvertently inhibited. In one embodiment of the present invention a dressing composition which has the ability to absorb the wound fluid and store it, would be particularly suitable.

Hydrogel polymers may be employed for this purpose. Hydrogels are natural or synthetic polymers which are highly absorbent and which, due to their high water content, have a degree of flexibility similar to that of natural tissue. Polyvinylpyrrolidone (PVP), acrylamide gels and poly(2-hydroxyethyl methacrylate) (pHEMA) are all examples of hydrogels. In a preferred embodiment of the present invention, the wound dressing composition polymer is a hydroxyalkyl ester of acrylic or methacrylic acid. In a particularly preferred embodiment the dressing composition polymer is a hydrogel comprising poly(2-hydroxyethyl methacrylate). More preferably, the wound dressing polymer is a hydrogel comprising poly(2-hydroxyethyl methacrylate) and poly(ethylene glycol) (PEG).

Any inhibitor of MMP's may be suitable for covalent attachment to the wound dressing for use in treating chronic wounds. Examples of such inhibitors include but are not limited to cation chelators, such as ethylenediaminetetraacetic acid (EDTA), tetracyclines and their derivatives, hydroxamic acids and bisphosphonates.

Bisphosphonates exhibit low toxicity and have been well tolerated for several years of human use, primarily in the management of calcium and bone metabolism disorders. In a preferred embodiment of the present invention the MMP inhibitor attached to the wound dressing is a bisphosphonate. Non-limiting examples of such bisphosphonates are etidronate, clodronate, tiludronate, pamidronate, neridronate, olpadronate, alendronate, ibandronate, risedronate, zoledronate, YH529, incadronate (YM175) and EB-1053.

For reasons of ease of manufacture of the dressing composition which will be discussed later it is particularly preferred that the bisphosphonate immobilized onto the polymer is an amino-bisphosphonate. Non-limiting examples include alendronate, pamidronate, neridronate or incadronate.

Given the inventor's discovery that MMP-9 is the predominant protease responsible for collagen degradation in chronic wound fluid it is particularly desirable to choose an MMP inhibitor which is a specific inhibitor of MMP-9. This should have a desirable effect in optimally inhibiting the proteolytic environment of the wound fluid. One non-limiting example of such an MMP-9 specific inhibitor is alendronate. In a preferred embodiment, alendronate is the MMP-inhibitor attached to the wound dressing composition of the present invention.

Another example of an MMP inhibitor is an anti-MMP antibody.

In this regard, anti-MMP-9 monoclonal antibodies are commercially available (eg. mouse mAb 606B from Calbiochem™) and are also described in Symowicz et al, 2007, Cancer Res. 67 2030 and Andrews et al., 2000, Am. J. Pathol. 157 303.

The invention also provides a method of producing an MMP inhibitor-monomer conjugate including the step of coupling an MMP inhibitor with a monomer to thereby form an MMP inhibitor-monomer conjugate. If required, the MMP inhibitor-monomer conjugate can then be incorporated into the polymer of the dressing composition.

In one particular embodiment, a method of producing an MMP inhibitor-methacrylate conjugate including the step of coupling an MMP inhibitor with a methacrylate monomer to thereby form an MMP inhibitor-methacrylate conjugate, is provided.

One example of this type of reaction is shown in FIG. 1. The reaction to form the conjugate is further discussed below.

In another aspect the invention resides in a method of producing a dressing composition including the step of covalently bonding a bisphosphonate to a polymer to thereby produce said dressing composition.

In one embodiment the bisphosphonate is first covalently bound to a monomer which is incorporated into the polymer. The invention therefore includes a method of producing a dressing composition including the steps of:

a) coupling the MMP inhibitor with a monomer to form an MMP inhibitor-monomer conjugate; and
b) incorporating the MMP inhibitor-monomer conjugate into a polymer to thereby produce a dressing composition.

The monomer employed to form the MMP inhibitor-monomer conjugate may be selected from a wide range of suitable monomers. Non-limiting examples are acrylates, methacrylates, vinyl sulfones or poly(ethylene glycol) (PEG) aledhydes. Acrylates and methacrylates are particularly useful and in one preferred embodiment the monomer chosen is a methacrylate monomer.

The particular monomer employed will be selected on the basis of two functionalities which it must present or be capable of being modified to present. The first is the functional group which will react with the bisphosphonate to covalently couple the two together and the second is the functional moiety presented to enable the MMP inhibitor-monomer conjugate to be incorporated into the polymer by means of another covalent bond, if required.

Some examples of useful functional groups which may be displayed by the above-identified monomers for the purpose of reacting with the MMP inhibitor are carboxylic acids, acid halides, aldehydes, ketones, epoxides, sulfonyls and succinimides such as N-hydroxysuccinimide and malimide. These functionalities are particularly susceptible to nucleophilic attack by moieties such as a hydroxy or amino group presented by the bisphosphonate.

An available double bond, e.g. a vinyl group, presented on the monomer has been found to be particularly suitable for subsequent incorporation of the MMP inhibitor-monomer conjugate into the polymer of the dressing composition.

It will be appreciated that the functionalities discussed in relation to the monomer may actually be presented by the bisphosphonate and vice versa. The important point is that the two are able to react to form a covalent bond and present the necessary functionality to be incorporated into the polymer.

In one preferred embodiment the monomer chosen is methacryloyl chloride which presents the highly reactive acid chloride functionality for coupling with the nucleophile of the bisphosphonate and a vinyl group for polymerisation with the polymer component monomers.

Advantageously, more than one MMP inhibitor may be attached to the one wound dressing. This may be useful when more than one sub-type of protease is being specifically targeted for inhibition. To achieve this, separate compositions of inhibitors and/or inhibitor-monomer conjugates would be prepared. These compositions would then be combined before initiating the polymerisation reaction to form the wound dressing composition. If the functionalities of the inhibitors or conjugates differ, then the polymers or reaction conditions should be chosen carefully to ensure there will be no adverse or side reactions.

The exact mechanism of coupling the MMP inhibitor to the monomer to form the MMP inhibitor-monomer conjugate will vary depending on the particular inhibitor/s and monomer chosen.

In one preferred embodiment, when the MMP inhibitor is alendronate then, as discussed, the monomer chosen for conjugation is methacryloyl chloride. The reaction of these compounds is demonstrated in FIG. 1 wherein the primary amine of alendronate reacts with the acid chloride functionality of the methacryloyl chloride to give an amide linkage. An amide linkage is particularly desirable as it is not easily cleaved by naturally occurring enzymes compared to, for example, ester linkages. So long as the MMP inhibitor chosen can react with the functionality present on the monomer then that monomer may be useful in the wound dressing of the present invention but a combination of MMP inhibitor and monomer functionality which react to form a strong and stable covalent bond, such as an amide bond, will be preferred. In short, the formation of any bond which is unlikely to be hydrolysed or otherwise cleaved to any great extent under physiological conditions in the wound fluid is particularly preferred in the attachment of the MMP inhibitor to the monomer to form the conjugate and/or to the polymer.

As mentioned, the conjugate produced by the reaction of the methacryloyl monomer with the MMP inhibitor will normally have a functionality which then allows its incorporation into a polymer. In the example shown in FIG. 1 this functionality is an alkene moiety (in this case a vinyl group). This is suitable for reaction by irradiation with the available double bond of 2-hydroxyethyl methacrylate (HEMA) monomers during the polymerisation reaction. The final polymer with the covalently bound alendronate incorporated is then formed, as shown in FIG. 1.

This combination of alendronate and methacryloyl chloride to form the conjugate and its incorporation into pHEMA is a particularly favourable approach. Alendronate presents a free amine functionality which is conveniently reacted with the acid chloride of methacryloyl chloride without the necessity for any modifications or functional group transformations prior to the reaction. This provides a conjugate with the alendronate and methacrylate joined by an amide bond which is particularly stable to hydrolysis or enzymatic cleavage under the physiological conditions found in chronic wound fluid. This conjugate can then be introduced to the HEMA, which forms a particularly useful hydrogel, and the polymer with incorporated conjugate formed in a single irradiation step. Thus a stable and superabsorbent dressing composition having a covalently bound bisphosphonate (alendronate) which targets the predominant MMP in the wound fluid responsible for collagen degradation (MMP-9) is formed in a minimal number of steps.

It is advantageous to focus the inhibitory activity of the dressing composition on the main MMP responsible for the undesirable proteolytic activity in the wound fluid (MMP-9, as shown by the inventors). This ensures that the bound therapeutic is all targeted towards minimising the damage caused by this MMP and thereby giving the wound the best chance of healing. It also further lessens the likelihood of the activity of other MMP's which are necessary for normal healing from being substantially reduced since a targeted approach is employed.

Depending on the MMP inhibitor chosen and the polymer used to form the wound dressing, it may be possible to incorporate the MMP inhibitor directly into the polymer without first reacting it with a methacryloyl monomer. For example the functional groups described above as suitable for the monomers may be presented directly by the polymer or its constituent monomers prior to polymerisation. Also, if the functionality required for polymerisation is not an alkene then a different kind of monomer may be used which has the necessary functionality and also the ability to couple to the inhibitor.

The examples section sets out the methodology to create a wound dressing according to one preferred embodiment of the invention. In this example poly(ethyleneglycol) (PEG) with an average molecular weight of 20,000 is included in the composition to form the polymer. The PEG is not an essential element and may not be chemically bound to the cross linked pHEMA. It is present as an additive to improve the physical characteristics and biocompatibility of the resulting hydrogel.

PEG may be present in the wound dressing composition in a percentage range from 10% to 80% by weight. Preferably, PEG is present in the wound dressing composition in a percentage range from 20% to 60% by weight. More preferably, PEG is present in the wound dressing composition in a percentage range from 25% to 40% by weight. Even more preferably, PEG is 30% by weight of the wound dressing composition.

Other additives may be present in the wound dressing composition to improve a variety of physical properties of the resulting wound dressing such as its physical strength, density, swelling characteristics i.e. improved ability to absorb wound fluid, biocompatibility and the like. Such additives are commonly employed in polymer chemistry and other fields and would be well known to the skilled addressee.

The example describes pHEMA as the polymer into which the alendronate is chemically incorporated. Any polymer into which the MMP inhibitor can be incorporated and which can act as or be made into a wound dressing would be within the scope of the present invention. Traditional cloth wound dressings may be adequate but, as mentioned previously, hydrogel polymers are preferred for their absorbent properties.

Any monomer which has the properties of a hydrogel when polymerised may be suitable for inclusion into the wound dressing composition of the present invention. Preferably, the monomers used to form the polymer are 2-hydroxyethyl methacrylate (HEMA) monomers.

Depending on the properties which the hydrogel is desired to have, the percentage by weight amount of HEMA monomers in the pre-polymerisation wound dressing composition may be from 5% to 80% by weight. Preferably, the HEMA monomers are present from 10% to 60% by weight. More preferably, the HEMA monomers are present from 15% to 40% by weight. Even more preferably, the HEMA monomers form 20% by weight of the wound dressing composition.

The choice of solvent in which to make up the wound dressing composition will depend on the nature of the monomers chosen for the polymerisation reaction. Organic and aqueous solutions may be suitable. In one preferred form the solvent chosen is water.

Another aspect of the invention resides in an MMP inhibitor-methacrylate conjugate comprising an MMP inhibitor coupled to a methacrylate monomer.

The dressing compositions of the present invention will normally be formulated as already described. In one embodiment however, the incorporation into a polymer is not carried out. This leaves the MMP inhibitor-methacrylate conjugate. This conjugate may be used to treat wounds by any number of means which result in the MMP inhibitor coming into contact with MMP's in the wound fluid but not being released into the wound tissue. Incorporation into a polymer to form a wound dressing as described in the examples is merely one, non-limiting way of administering the bound MMP inhibitor.

The invention also resides in a dressing, implant or prosthesis with an MMP inhibitor-monomer conjugate coupled thereto. A preferred conjugate is an MMP inhibitor-methacrylate conjugate.

As mentioned above, the MMP inhibitor-monomer conjugate may be attached to a range of other devices than a wound dressing, such as an implant or prosthesis. These devices would, as with the dressing, allow the MMP inhibitor to contact the wound fluid without releasing the inhibitor into the wound tissue to any great extent.

Yet another aspect of the invention resides in a method of selectively inhibiting an MMP within a wound fluid without inhibiting an MMP within a wound tissue, in a patient in need of such treatment, including the step of contacting the wound fluid with an MMP inhibitor covalently bound to a polymer in a dressing composition to thereby selectively inhibit said MMP within the wound fluid without inhibiting said MMP within the wound tissue.

In one embodiment the MMP inhibitor is a bisphosphonate.

Preferably, the MMP inhibitor is alendronate.

Suitable polymers and means of immobilising the MMP inhibitor either directly to the polymer or via a monomer are as previously described.

Preferably, the patient being treated is a mammal such as, but not limited to, humans, livestock, performance animals and pets.

More preferably, the patient is a human.

Preferably, the MMP within the wound fluid which is being inhibited is MMP-9.

As previously described, the treatment of a wound should include the use of an MMP inhibitor to reduce the proteolytic content of the wound fluid but it is undesirable to inhibit the MMP's in the wound tissue at the same time as they have important roles to play in normal wound healing.

In a preferred embodiment the MMP inhibitor is delivered as part of a dressing composition. It should be understood that any means of delivering the bound MMP inhibitor to the wound fluid which does not also allow it to enter the wound tissue would be within the scope of the present invention.

It is contemplated that an MMP inhibitor could also be delivered by way of a polymer spray. In one particular embodiment, the polymer spray could be applied so as to form a polymer layer, film or sponge comprising said MMP inhibitor in situ. Ointments or creams comprising a polymer which set such that the MMP inhibitor is not released into the wound tissue are also dressing compositions considered within the scope of the present invention.

A particular advantage of polymer films relates to the fact that chronic wounds are often stalled in the inflammatory phase. This could be modulated via an amino-bisphosphonate tethered to a polymer film, for example, so that the layer of the polymer film that comes in contact with the wound bed could modulate inflammation. This may also minimise biofilm formation that is a result of excessive inflammation and up-regulation of the immune response.

The invention also resides in a method of therapeutic treatment of a wound in an animal including the step of administering a wound dressing composition as hereinbefore described, to the animal.

The chronic wounds particularly suitable for treatment with the dressing composition of the present invention are any wounds that do not heal by following the orderly set of stages and within the normal time line of most acute wounds. The vast majority of chronic wounds can be classified into the three categories of venous ulcers, diabetic ulcers and pressure ulcers. These chronic wounds may take years to heal or may never do so.

Figure 2:
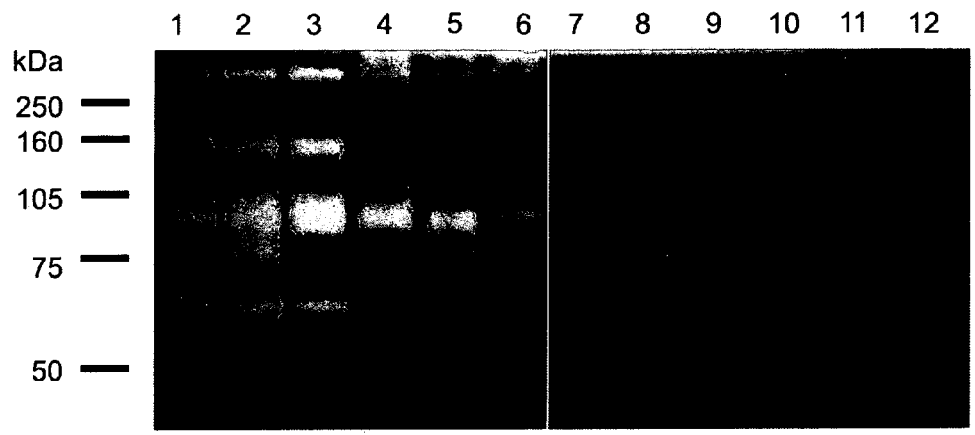
FIG. 2 shows the results of a Collagen Type 1 zymography assay of six chronic wound fluid samples before and after incubation with alendronate.

The examples section sets out the efficacy of alendronate as an MMP inhibitor. In FIG. 2, protease activity is seen on the assays as clear bands against a dark background and the bands can be seen in lanes 1-6 which are samples of chronic wound fluid from six different patients. This clearly shows the proteolytic environment in the wound fluid. Lanes 7-12 represent the same fluid samples after incubation with alendronate. The protease activity has been greatly reduced as demonstrated by the decrease in the number and intensity of clear bands which are visible. Bisphosphonates, and in particular alendronate, are therefore a suitable class of wound fluid MMP inhibitors for use in the wound dressing of the present invention. It is believed that these results with alendronate are particularly impressive as it inhibits MMP-9, identified by the inventors as the predominant protease acting on collagen formation. A specific inhibitor of an MMP which is not particularly active in the degradation of collagen in wound fluid would clearly not present such excellent results and so this targeted approach is preferred.

It is an advantage of the present invention that the MMP inhibitor is covalently attached to the wound dressing so that substantially all of it remains immobilised. In this manner, again, MMP's in the wound fluid are inhibited, suppressed, inactivated or have their activity in some way reduced to a greater extent than those MMP's in the wound tissue.

Not only does this prevent active MMP's in the wound tissue which are useful for normal healing from being inhibited but it also reduces or even eliminates any potential side effects from the MMP inhibitor. For example, tetracyclines and their analogues have been employed as MMP inhibitors but they demonstrate a number of undesirable side effects such as gastrointestinal disturbances and potential antibiotic resistance problems.

Since other prior art treatments consider making the MMP inhibitor available systemically, or at least do not prevent it from diffusing into the tissues or circulatory system, then these side effects can be a real problem. The wound dressing of the present invention has substantially all of the MMP inhibitor remaining attached and so avoids the problem of any potential side effects which the MMP inhibitor employed may have.

A further advantage of the present invention is that it provides a simplified treatment regime for patients with chronic wounds. Having the therapeutic treatment incorporated into the wound dressing avoids the need for oral, intravenous, topical administration etc. The wound will generally be covered anyway so it is convenient and time saving to include the therapeutic molecule within the dressing composition.

The wound dressing composition of the present invention may be provided as the sole treatment for a patient with a chronic wound or it may be used in combination with other existing therapies to improve the healing state of the wound. The wound dressings may be applied until the wound has healed or at least an improvement in its healing state has been observed. Since the MMP inhibitor is not released into the wound tissue its dosage does not have to be regulated by a healthcare professional. The wound dressings can be used for as long as is desirable.

Another advantage is provided by the wound dressing composition of the invention. Typically, wound dressings adsorb wound fluid which may contain proteases. Hence if protease-susceptible therapeutic agents such as growth factors, antimicrobial agents, drugs, antibiotics are being delivered concomitantly via the wound dressing, then an MMP inhibitor present in the dressing may inactivate or reduce the activity of proteases away from the wound bed and will prevent or minimize the destruction of these therapeutics and lessen the release of proteolysis products into the wound bed.

So that the invention may be readily understood and put into practical effect reference is made to the following non-limiting Examples.

EXAMPLES

MMP Inhibition with Alendronate

Since the inventors have identified that MMP-9 is the predominant protease involved in degrading the extracellular matrix in chronic wound fluid, a bisphosphonate was tested for its ability to inhibit MMP, particularly MMP-9, activity. Alendronate (as its sodium salt) was chosen as the representative bisphosphonate.

Alendronate sodium salt was incubated with chronic wound fluid samples at a concentration of 2 mM, at 37° C., for 24 hours. Collagen Type 1 zymography was then employed to identify protease activity. Collagenase sensitivity was identified as clear bands against a dark background in zymograms and could be quantitated by densitometric analysis.

FIG. 2 shows the results of this assay. Lanes 1-6 are chronic wound fluid samples from six different patients with 500 ng of total protein loaded per sample. Lanes 7-12 represent the same chronic wound fluid samples 1-6 with 500 ng of total protein loaded per sample after incubation with 2 mM alendronate at 37° C. for 24 hours.

The large reduction in protease activity after incubation with alendronate is clearly visible. This proves that bisphosphonates, and particularly alendronate, are effective inhibitors of MMP's and so have the potential to neutralise the excessively proteolytic environment present in chronic wounds and modulate them towards a healing state.

Alendronate Conjugate Formation and Hydrogel Incorporation

As shown in FIG. 1, wherein the bisphosphonate is alendronate, the primary amine group of alendronate can be reacted with the acid chloride functionality of methacryloyl chloride. This will provide a conjugate which presents the alendronate and also has an alkene functionality to allow incorporation into a polymer which, in FIG. 1, is a pHEMA hydrogel polymer.

To achieve this, alendronate sodium salt (300 mg, 0.92 mmol) was dissolved in aqueous NaOH (148 mg, 3.70 mmol in 7.4 mL $H_2O$) with 4-methoxy phenol to inhibit polymerisation. The solution was cooled in an ice-salt bath before the addition of freshly distilled methacryloyl chloride (120 mg, 1.15 mmol) and NaOH (111 mg, 2.768 mmol in 5.5 mL $H_2O$) stepwise, maintaining the pH above 11. The reaction was stirred vigorously for 20 hours before being acidified to pH 7 with HCl. The resulting product was evaporated to dryness and extracted with chloroform to remove any impurities. The water layer was then precipitated with DMF to obtain the alendronate-methacrylate conjugate in 49% yield.

An aqueous solution is then prepared of distilled 2-hydroxyethyl methacrylate (HEMA) and PEG 20,000 in the approximate ratio of 50% water: 30% PEG: 20% HEMA. A suitable concentration of the alendronate/methacryloyl conjugate is then added e.g. 20 mM. The solutions were then placed between two glass plates separated by a silicone gasket and purged with argon.

The moulds were then gamma irradiated with a Gamma-cell 220 using a $^{60}Co$ source to give a total dose of between 5 kGY to 10 kGy. Polymerisation was characterised using NIR FT-Raman Spectroscopy which demonstrated complete polymerisation of the HEMA monomer to its polymer form (pHEMA) and thereby ensures that no alendronate could be released from the hydrogel. This was ascertained by identifying the change in the characteristic C=C peak at 1639 $cm^{-1}$.

Characterisation of Wound Dressing MMP Inhibitory Action

A functional collagen degrading assay can be employed to analyse the ability of the synthesised bisphosphonate containing hydrogels to inhibit MMP's in chronic wound fluid.

As above, a pooled sample of chronic wound fluid was run on Collagen Type I zymograms using Collagen Type I at a final concentration of 0.5 mg/mL in 10% total acrylamide gels under non-reducing conditions. Electrophoresis was performed at 4° C. under Laemmli conditions. The gels were then washed in 2.5% Triton X-100 for 30 min, then a further 60 min, prior to incubation in 50 mM Tris-HCl, $CaCl_2$ (10 mM) and NaCl (50 mM) at pH 7.6 for 24 hours at 37° C. Alendronate functionalised hydrogels (as prepared above) were cut into small pieces and included in the incubation buffer and then incubated at 37° C. for 24 hours. Two concentrations, 2 mM and 20 mM, of the equivalent bisphosphonate segment of alendronate-methacrylate in the monomer solution were used to make two separate hydrogels. The zymography was also run for just the alendronate-methacrylate conjugate at 2 mM.

The proteases in the chronic wound fluid were immobilised in the substrate gels and then exposed to the inhibitor while they were active in the 37° C./24 h incubation step. After incubation the gels were stained appropriately and protease activity was visualised as clear (unstained) bands.

Figure 3:
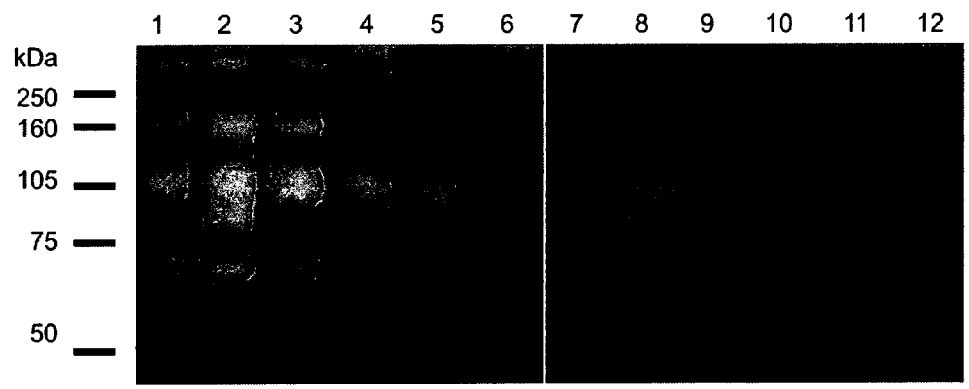
FIG. 3 shows the results of a Collagen Type 1 zymography assay of six chronic wound fluid samples before and after incubation with an alendronate-methacrylate conjugate.

FIG. 3 indicates that the alendronate-methacrylate conjugate was able to inhibit MMP's at a physiological temperature over a 24 hour period. Lanes 1-6 in FIG. 3 are chronic wound fluid samples (500 ng protein) from six different patients, as for FIG. 2. Lanes 7-12 represent the same samples after incubation with 2 mM of the alendronate-methacrylate conjugate shown in FIG. 1. The inhibitory activity was at a slightly reduced level compared to that of alendronate alone.

Figure 4:
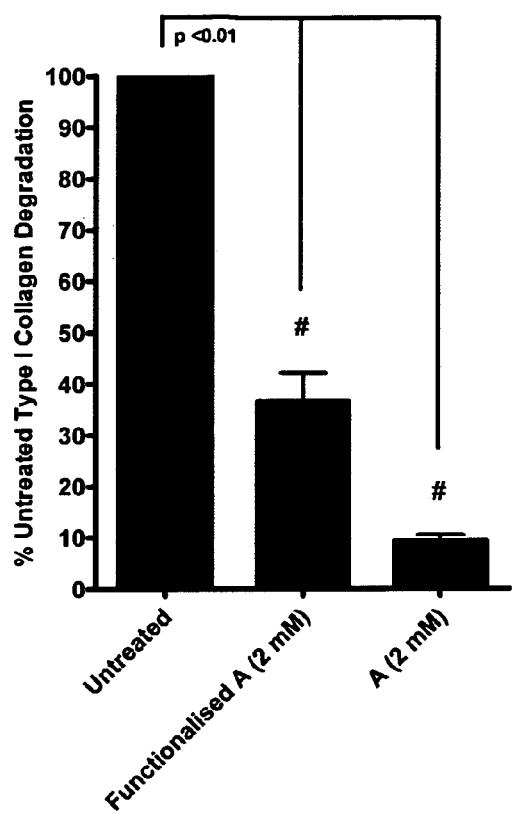
FIG. 4 is a representation of the relative reduction in protease activity obtained by inhibition with alendronate and an alendronate-methacrylate conjugate compared to an untreated control.

FIG. 4 is a representation of the relative reduction in protease activity obtained by inhibition with alendronate and an alendronate-methacrylate conjugate compared to an untreated control and so represents the results shown in FIGS. 2 and 3. Densitometry was used to quantify the reduction in proteolytic activity demonstrated by the zymography and this is represented graphically in FIG. 4. The MMP specific inhibition of collagen degrading activity is shown for the alendronate-methacrylate conjugate (marked Functionalised A 2 mM) and alendronate itself (marked A 2 mM) compared to the untreated control samples. Statistical significance is relative to the untreated samples and is shown as # ($p<0.01$) as determined by Tukey's test.

FIG. 4 demonstrates that, when treated with alendronate at 2 mM the type I collagen degradation is 10% or less of that seen in the untreated control. The alendronate-methacrylate conjugate is between 30%-40% of that seen in the control and so represents a very significant level of inhibition of collagen degradation.

The hydrogels containing the alendronate-methacrylate conjugate also demonstrated good levels of MMP inhibition. The hydrogel containing 20 mM of alendronate-methacrylate displayed the ability to significantly reduce Collagen Type I degradation as compared with a non-hydrogel treated control.

Figure 5:
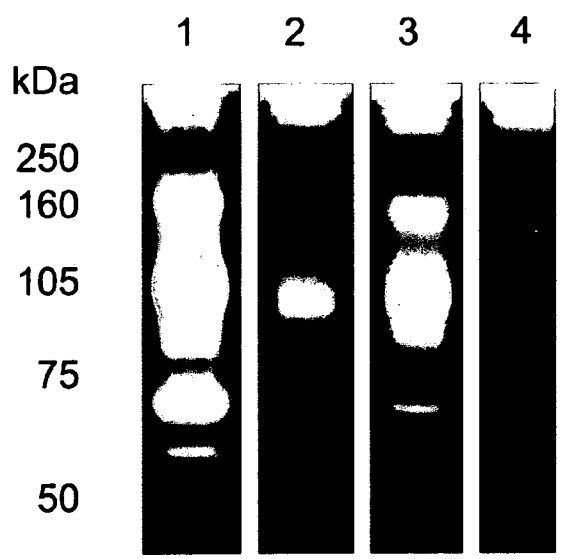
FIG. 5 shows the results of a Collagen Type 1 zymography assay of a chronic wound fluid sample before and after incubation with polymers incorporating covalently bound alendronate.

FIG. 5 shows the results of a Collagen Type I zymography assay of a chronic wound fluid sample before and after incubation with hydrogel polymers incorporating covalently bound alendronate. Three different hydrogel samples were generated and used in this assay. All hydrogels were synthesised as described above using 5.0 g H$_2$O, 2.0 g HEMA and 3.0 g of PEG 20,000. The first sample (denoted 'G' in FIG. 6) had only these components with no bisphosphonate and so acted as a hydrogel control. The second (denoted 'GA1X' in FIG. 6) hydrogel sample further comprised 7.68 mg of the alendronate-methacrylate conjugate and the third sample (denoted 'GA10X' in FIG. 6) contained 76.80 mg of the alendronate-methacrylate conjugate.

In FIG. 5, lane 1 is the pooled chronic wound fluid sample without any inhibitor while lanes 2 to 4 show the same fluid sample with hydrogels G, GA1X and GA10X, respectively, cut into small pieces and incubated at 37° C. for 24 hours. While the control hydrogel and 2 mM alendronate-methacrylate conjugate both reduced the proteolytic activity it is clear from the disappearance of most of the clear bands that the 20 mM conjugate (GA10X) was the most effective sample.

Figure 6:
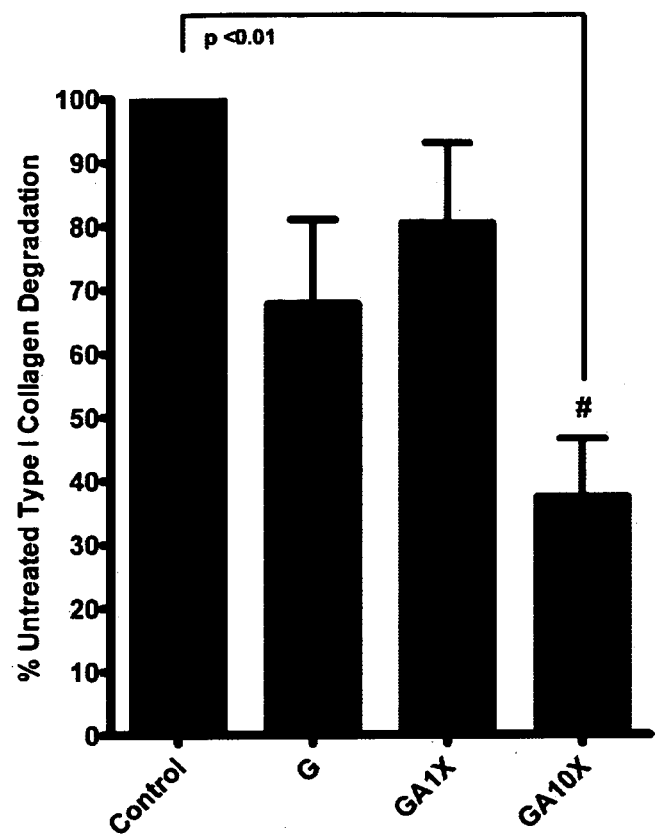
FIG. 6 is a representation of the relative reduction in protease activity obtained by inhibition with polymers incorporating covalently bound alendronate compared to an untreated control.

FIG. 6 is a representation of the relative reduction in protease activity obtained in the experiment shown in FIG. 5. FIG. 6 was generated in a manner as described for FIG. 4.

FIG. 6 demonstrates that the hydrogel sample without alendronate (sample 'G') has the ability to inhibit MMP's to some extent. This is a further advantage of employing this type of polymer in the dressing compositions of the present invention. Although not wishing to be bound by any particular theory the inventors postulate that this may be due to the three oxygen atoms presented in the HEMA monomer which would be available for chelation with the cations which the MMP's require for their stability.

FIG. 6 further shows that the 2 mM (GA1X) hydrogel-conjugate sample demonstrates inhibitory activity but the 20 mM sample (GA10X) displays a greater level of activity and effectively demonstrates the efficacy of a bisphosphonate tethered to a hydrogel as part of a wound dressing composition in the treatment of chronic wounds.

The dressing compositions of the present invention comprising a bisphosphonate covalently bound to a polymer can, therefore, be successfully employed to inhibit MMP's in the wound fluid.

It will be appreciated by the skilled person that the present invention is not limited to the embodiments described in detail herein, and that a variety of other embodiments may be contemplated which are, nevertheless, consistent with the broad spirit and scope of the invention.

All computer programs, algorithms, patent and scientific literature referred to in this specification are incorporated herein by reference in their entirety.

The invention claimed is:

1. A dressing composition comprising a bisphosphonate, or a pharmaceutically acceptable salt thereof, covalently bound to a hydrogel polymer wherein, when the dressing is contacted with a wound, substantially all of the bisphosphonate, or a pharmaceutically acceptable salt remains with the dressing and is unable to enter a wound tissue, wherein the hydrogel polymer comprises a hydroxyalkyl ester of acrylic or methacrylic acid.

2. The dressing composition of claim 1 wherein the bisphosphonate is an amino-bisphosphonate.

3. The dressing composition of claim 2 wherein the amino-bisphosphonate is selected from the group consisting of alendronate, pamidronate, neridronate or incadronate.

4. The dressing composition of claim 1 comprising the bisphosphonate.

5. The dressing composition of claim 1 wherein the hydroxyalkyl ester of acrylic or methacrylic acid is poly(2-hydroxyethyl methacrylate).

6. The dressing composition of claim 5 wherein the hydrogel polymer further comprises poly(ethylene glycol).

7. The dressing composition of claim 1 wherein the bisphosphonate is covalently bound to a monomer which is covalently bound to the polymer.

8. The dressing composition of claim 7 wherein the monomer is selected from the group consisting of acrylates, methacrylates, vinyl sulfones or functionalized poly(ethylene glycol).

9. The dressing composition of claim 8 wherein the selected monomer presents a functional group selected from the group consisting of carboxylic acids, acid halides, aldehydes, ketones, epoxides, sulfonyls or succinimides.

10. The dressing composition of claim 9 wherein the monomer is methacryloyl chloride.

11. A method of selectively inhibiting a matrix metalloproteinase (MMP) within a wound fluid without inhibiting the MMP within a wound tissue, in a patient in need of such treatment, including the step of contacting the wound fluid with an MMP inhibitor covalently bound to a hydrogel polymer in a dressing composition to thereby selectively inhibit said MMP within the wound fluid without inhibiting said MMP within the wound tissue, wherein the hydrogel polymer comprises a hydroxyalkyl ester of acrylic or methacrylic acid, and wherein the MMP inhibitor comprises a bisphosphonate, or a pharmaceutically acceptable salt thereof.

12. The method of claim 11 or claim 9 wherein said MMP being inhibited within the wound fluid is MMP-9.

13. The method of claim 11 wherein the patient is a mammal.

14. The method of claim 13 wherein the mammal is a human.

15. A method of producing a dressing composition including the step of covalently bonding a bisphosphonate to a polymer to thereby produce said dressing composition, wherein the polymer comprises a hydroxyalkyl ester of acrylic or methacrylic acid.

16. The method of claim 15 wherein the bisphosphonate is covalently bound to a monomer which is incorporated into the polymer by irradiation.

17. The dressing composition of claim 1 wherein the wound tissue is a chronic wound.

18. The dressing composition of claim 1 being formulated to absorb and store wound fluid associated with the wound tissue.

* * * * *